United States Patent
Stanley et al.

(10) Patent No.: US 6,261,595 B1
(45) Date of Patent: Jul. 17, 2001

(54) TRANSDERMAL DRUG PATCH WITH ATTACHED POCKET FOR CONTROLLED HEATING DEVICE

(75) Inventors: Theodore Stanley, Salt Lake City; Wade Hull, Taylorsville; Larry Rigby, Salt Lake City, all of UT (US)

(73) Assignee: Zars, Inc., Salt Lake City, UT (US)

(*) Notice: Subject to any disclaimer, the term of this patent is extended or adjusted under 35 U.S.C. 154(b) by 0 days.

(21) Appl. No.: 09/515,722

(22) Filed: Feb. 29, 2000

(51) Int. Cl.[7] .............. A61F 13/00; A61L 15/16; A61N 1/30

(52) U.S. Cl. .............. 424/449; 424/448; 424/447; 604/20

(58) Field of Search .................. 424/449, 447; 604/20

(56) References Cited

U.S. PATENT DOCUMENTS

| | | | |
|---|---|---|---|
| D. 403,778 | 1/1999 | Davis et al. | D24/206 |
| D. 403,779 | 1/1999 | Davis et al. | D24/206 |
| D. 407,822 | 4/1999 | Davis et al. | D24/206 |
| D. 407,824 | 4/1999 | Davis et al. | D24/206 |
| D. 408,923 | 4/1999 | Davis et al. | D24/206 |
| D. 409,757 | 5/1999 | Davis et al. | D24/206 |
| D. 412,751 | 8/1999 | Davis et al. | D24/206 |
| D. 417,283 | 11/1999 | Davis et al. | D24/206 |
| D. 418,606 | 1/2000 | Davis et al. | D24/206 |
| 3,929,131 | 12/1975 | Hardwick | 128/254 |
| 4,210,670 | 7/1980 | Cooke | 424/324 |
| 4,230,105 * | 10/1980 | Harwood | 128/156 |
| 4,286,592 | 9/1981 | Chandrasekaran | 128/260 |
| 4,529,601 | 7/1985 | Broberg et al. | 514/626 |
| 4,685,911 | 8/1987 | Konno et al. | 604/897 |
| 4,693,706 | 9/1987 | Ennis, III | 604/87 |
| 4,747,841 * | 5/1988 | Kuratomi et al. | 604/291 |
| 4,830,855 | 5/1989 | Stewart | 424/448 |
| 4,898,592 | 2/1990 | Latzke et al. | 604/307 |
| 4,911,707 | 3/1990 | Heiber et al. | 424/449 |
| 4,913,957 * | 4/1990 | Strack et al. | 428/286 |
| 4,963,360 * | 10/1990 | Arguad | 424/443 |
| 4,994,049 | 2/1991 | Latzke et al. | 604/307 |
| 5,108,710 | 4/1992 | Little et al. | 422/104 |
| 5,114,411 | 5/1992 | Haber et al. | 604/203 |

(List continued on next page.)

FOREIGN PATENT DOCUMENTS

| | | |
|---|---|---|
| 2 163 956 | 3/1988 | (GB) . |
| 88/09169 | 12/1988 | (WO) . |
| WO 97/01310 | 1/1997 | (WO) . |

(List continued on next page.)

OTHER PUBLICATIONS

Arky, et al., *Physicians' Desk Reference*, 1997, pp. 1336–1340.

Mack Publishing Company, "Stability of Pharmaceutical Products," *Pharmaceutical Sciences*, pp. 1481–2, 1985.

(List continued on next page.)

*Primary Examiner*—Thurman K. Page
*Assistant Examiner*—Isis Ghaci
(74) *Attorney, Agent, or Firm*—Kirton & McConkie; Michael F. Krieger (57) ABSTRACT

The present invention relates to a transdermal drug delivery system comprising a dermal drug delivery patch and a heating element compartment securable to the dermal drug delivery patch. A freely transferrable heating element is securable within the heating element compartment. A drug can be administered transdermally using the present invention by placing the dermal drug delivery patch upon a patient's skin at an administration site. A heating element compartment is secured to the dermal drug delivery patch and a freely transferrable heating element is placed within the heating element compartment. The heating element provides controlled heat to the dermal drug patch and the patient's skin aid thereby improves dermal drug administration.

52 Claims, 6 Drawing Sheets

U.S. PATENT DOCUMENTS

| | | | |
|---|---|---|---|
| 5,128,137 | 7/1992 | Miller et al. | 424/449 |
| 5,147,339 | 9/1992 | Sundstrom | 604/307 |
| 5,213,129 | 5/1993 | Someah et al. | 137/101.11 |
| 5,229,133 | 7/1993 | Wright et al. | 424/473 |
| 5,276,032 | 1/1994 | King et al. | 514/239.2 |
| 5,279,594 | 1/1994 | Jackson | 604/265 |
| 5,329,976 | 7/1994 | Haber et al. | 141/25 |
| 5,330,452 | 7/1994 | Zook | 604/307 |
| 5,364,350 | 11/1994 | Dittmann | 604/89 |
| 5,466,217 | 11/1995 | Myers et al. | 604/24 |
| 5,534,021 | 7/1996 | Dvoretzky et al. | 607/112 |
| 5,580,573 | 12/1996 | Kydonieus et al. | 424/449 |
| 5,605,536 | 2/1997 | Sibalis | 604/20 |
| 5,626,571 | 5/1997 | Young et al. | 604/370 |
| 5,651,768 | 7/1997 | Sibalis | 604/20 |
| 5,658,583 | 8/1997 | Zhang et al. | 424/402 |
| 5,662,624 | 9/1997 | Sundstromm et al. | 604/291 |
| 5,728,057 | 3/1998 | Ouellette et al. | 602/62 |
| 5,728,058 | 3/1998 | Ouellette et al. | 602/62 |
| 5,728,146 | 3/1998 | Burkett et al. | 607/109 |
| 5,733,255 | 3/1998 | Dinh et al. | 604/20 |
| 5,735,889 | 4/1998 | Burkett et al. | 607/96 |
| 5,741,318 | 4/1998 | Ouellette et al. | 607/108 |
| 5,837,005 | 11/1998 | Viltro et al. | 607/112 |
| 5,860,945 | 1/1999 | Cramer et al. | 602/62 |
| 5,904,710 | 5/1999 | Davis et al. | 607/108 |
| 5,906,637 | 5/1999 | Davis et al. | 607/108 |
| 5,906,830 | 5/1999 | Farinas et al. | 424/448 |
| 5,919,479 * | 7/1999 | Zhang et al. | 424/449 |
| 5,925,072 | 7/1999 | Cramer et al. | 607/108 |
| 5,980,562 | 11/1999 | Ouellette et al. | 607/108 |
| 5,984,995 | 11/1999 | White | 75/230 |
| 6,019,782 | 2/2000 | Davis et al. | 607/96 |
| 6,020,040 | 2/2000 | Cramer et al. | 428/64.1 |
| 6,024,761 | 2/2000 | Barone et al. | 607/108 |
| 6,042,673 | 3/2000 | Johnson et al. | 156/227 |
| 6,048,326 | 4/2000 | Davis et al. | 602/26 |

FOREIGN PATENT DOCUMENTS

| | | |
|---|---|---|
| WO 97/01311 | 1/1997 | (WO) . |
| WO 97/01312 | 1/1997 | (WO) . |
| WO 97/01313 | 1/1997 | (WO) . |
| WO 97/36968 | 10/1997 | (WO) . |
| WO 97/49361 | 12/1997 | (WO) . |
| WO 98/28021 | 7/1998 | (WO) . |
| WO 98/28024 | 7/1998 | (WO) . |
| WO 98/29063 | 7/1998 | (WO) . |
| WO 98/29064 | 7/1998 | (WO) . |
| WO 98/29065 | 7/1998 | (WO) . |
| WO 98/29067 | 7/1998 | (WO) . |
| WO 98/29066 | 9/1998 | (WO) . |
| WO 99/09917 | 3/1999 | (WO) . |
| WO 99/09918 | 3/1999 | (WO) . |

OTHER PUBLICATIONS

McCafferty, et al., "Comparative In Vivo and In Vitro Assessment of the Percutaneous Absorption of Local Anaesthetics," *British Journal of Anaesthesia*, vol. 60, (1988), 64–69.

Woolfson, et al., "Concentration Response Analysis of Percutaneous Local Anaesthetic Formulations," *British Journal of Anaesthesia*, vol. 61, (1988), pp. 589–592.

McCafferty, et al., "In Vivo Assessment of Percutaneous Local Anaesthetic Preparations," *British Journal of Anaesthesia*, vol. 62, (1989), pp. 17–21.

Knutson et al., "Solvent–Mediated Alterations of the Stratum Corneum," *Journal of Controlled Release*, vol. 11, (1990), pp. 93–103.

Lycka, "EMLA, A New and Effective Topical Anesthetic," *J. Dermotol, Surg. Oncol.*, vol. 18, (1992), pp. 859–862.

McCafferty, et al., "New Patch Delivery System for Percutaneous Local Anaesthesia," *British Journal of Anaesthesia*, vol. 71, (1993) pp. 370–374.

Woolfson, *Percutaneous Local Anaesthesia*, E. Horwood, N.Y. (1993), pp. 166–170.

"Room Temperature", Macmillan, U.S.A., *Webster's New World College Dictionary*, Third Edition, 1997, pp. 1165.

Florey, Klaus, *Analytical Profiles of Drug Substances*, vol. 15, 1986, pp. 150–231.

Florey, Klaus, *Analytical Profiles of Drug Substances*, vol. 12, 1983, pp. 73–105.

"Local Anesthetics, Parenteral, general Statement," *AHFS Drug Information*, 1992.

Florey, Klaus, *Analytical Profiles of Drug Substances*, vol. 18, 1989, pp. 379–411.

Sakamoto et al., "Dermal patch anesthesia: comparison of 10% lignocaine gel with absorption promotor and EMLA cream," *Anesthesia*, vol. 48, pp. 390–392.

Dvoretzky, Israel, M.D., "Hyperthermia Therapy for Warts Utilizing a Self–administered Exothermic Patch," *Dermal Surgery*, (1996), vol. 22, pp. 1035–1039.

Stern, Peter, M.D. and Levine, Norman, M.D., "Controlled Localized Heat Therapy in Cutaneous Warts," *Arch. Dermatol*, (Jul. 1992), vol. 128, pp. 945–948.

* cited by examiner

TRANSDERMAL DRUG PATCH WITH ATTACHED POCKET FOR CONTROLLED HEATING DEVICE

BACKGROUND

1. The Field of the Invention

The present invention is directed toward a method and apparatus for applying heat to a transdermal drug delivery system. More specifically, the invention is a securable compartment with a corresponding freely transferrable heating element for use with dermal drug delivery patches.

2. The Background Art

It has been discovered recently that the transdermal delivery of certain drugs can be facilitated by the application of heat. Controlled heat is provided to transdermal drug delivery patches using various techniques and apparatus such as heat generating patches. The heat generating patches sometimes utilize heat generated from chemical reactions, such as an oxidation reaction, or may utilize heat generated by an electrical current or some other method. One of the disadvantages of prior art heating apparatus for the transdermal drug patches is that the heating element must be secured to the transdermal patch without compromising the transdermal drug patch's attachment to the user's skin. In other words, sometimes when a user attempts to attach, replace, or adjust a heating patch or similar device, the drug delivery patch can become dislodged or otherwise made less secure. If the drug patch is not properly situated, the drug delivery system may be compromised. It is important in transdermal drug delivery that the skin be in contact with the formulation of the drug delivery patch to achieve efficient drug transfer.

Several methods for attaching or integrating a controlled heating element have been taught in the prior art. For example, wraps, adhesives, and tapes have all been suggested as potential ways for attaching a heating element to a patient's body or to a transdermal drug patch. Attempting to attach a heating element to a transdermal drug patch these ways has several disadvantages.

When a prior art adhesive technique is used to apply the heating element to the drug patch, the process of applying the heating element to the patch may cause the drug delivery patch to become less secure. To apply the heating element using adhesive, the areas of the heating element that contain the adhesive must be pressed firmly against the heating patch to secure the heating element to the patch. During this process, the drug delivery system may be unintentionally compromised.

In the event that the user needs to remove, replace or change the heating element, any attempts to remove the heating element may cause the adhesive of the transdermal patch to be compromised, and thus to compromise the drug delivery. The continued removal and replacement of the heating element may cause the transdermal drug patch to lose enough adhesive that the drug patch does not properly contact the skin and thereby become less effective and less secure.

A significant problem with using prior art wraps to secure a heating element to a transdermal drug patch is the potential for the heating element and/or the drug patch to become dislodged. If the heating element is secured using a wrap or tie, as the heating element is being tied to or wrapped into the user or the drug patch on the user, the process of tying or wrapping the heating element can cause the drug patch to lose contact with the skin of the patient and thereby compromise the drug delivery.

Another disadvantage of prior art teachings is the inconvenience associated with trying to remove a heating element that is attached by a wrap. In order to change or remove the heating element, the user must attempt to unwrap the heating element from the transdermal patch without disturbing the transdermal patch. This can be particularly difficult if the user needs to make the change quickly or if the patch is located in a position that makes delicately removing and replacing the heating element wrap impractical. For example, if the heating element were secured to a patch by a wrap that went around a patient's torso, frequent removal of the wrap could require substantial extra effort and work on the part of the patient and/or the user.

Another disadvantage of prior art teachings is the cost of integrating a heat element with a transdermal patch, particularly for heating elements that have limited uses and applications. If a patient requires a certain level of heating in one circumstance and a different level of heating in another, then the integrated patch must be removed and an entirely different patch with an appropriate heating level must be applied. Alternatives to this would require complex patch designs that attempt to control or modify the amount of heat generated by the heating element. Thus, using an integrated patch may increase manufacturing costs significantly. Moreover, modified and integrated designs may prove to be less reliable and may be prone to misuse.

Another disadvantage of the prior art is the potential for abuse where the heating element neither corresponds to a specific patch nor is integrated with a particular patch. If a heating patch can be freely used with any given transdermal device, there is a potential for the patch to be abused by a patient or misused by the user. For example, the patient may apply a heating element that induces an absorption rate that is too fast or delivers too much drug. Conversely, the user may apply a heating element that fails to supply sufficient heat for a particular treatment. Thus, where the patches do not correspond to the heating elements used with them, there is a potential for abuse or misuse.

BRIEF SUMMARY AND OBJECTS OF THE INVENTION

In view of the foregoing, it is an object of at least one embodiment of the present invention to provide a securable heating element compartment with corresponding freely transferrable heating element.

It Is another object of at least one embodiment of the present invention to provide a heating element advantageously secured to a transdermal drug patch.

It is another object of at least one embodiment of the present invention to provide a transdermal drug patch with a corresponding heating element pouch.

It is another object of at least one embodiment of the present invention to provide a heating element that is securely attached to but freely removable from a transdermal drug delivery patch.

It is another object of at least one embodiment of the present invention to provide a transdermal drug delivery patch and corresponding heating element that allows a heating element to be used to decrease the time necessary to reach steady state and that can be conveniently replaced with another heating element with different heating characteristics that provide different results, It is another object of at least one embodiment of the present invention to provide a transdermal drug delivery patch and corresponding heating element that can facilitate treatment of breakthrough pain, and/or that can be regulated to match the body's circadian rhythms, and/or that can provide additional booster drugs when necessary.

It is another object of at least one embodiment of the present invention to provide an electrical heating element advantageously and removably secured to a transdermal drug delivery patch.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention comprises a securable, heating element compartment with a corresponding, freely-transferrable heating element. The heating element compartment may be integrated with or secured to a transdermal drug delivery patch (drug patch). The heating element compartment provides an area of restraint that prevents the freely transferrable heating element from being displaced relative to the drug patch to which the heating element compartment is secured.

The freely transferrable heating element limits the likelihood that a drug patch will become dislodged or displaced during the placement, transfer, or replacement of the heating element. Thus, the freely transferrable heating element is secured proximate to a dug patch but, nevertheless, is easily removed and replaced with use in conjunction with the heating element compartment of the present invention. The heating element does not require an adhesive to be secured to the drug patch, nor does it need to he wrapped or otherwise tied to the patch or patient.

The heating element can be secured or retained in the area of restraint within the heating element compartment using the novel techniques disclosed herein, or alternatively, techniques known in the art. Novel techniques for restraining the freely transferrable heating element include using the top of the heating element compartment to provide tension and downward pressure upon a heating element within heating element compartment. Tension or downward pressure may be provided by sealing at least one edge (or a portion of an edge) of the top of the heating element compartment to create an area of restraint within the compartment disposing, a corresponding heating element within the heating element compartment. Because the heating element corresponds to the pouch either in relative shape or size (being approximately the same size and/or shape), the heating element fits snugly into the compartment and is secured within the heating element compartment in an area or restraint. The edge of the heating element compartment may be sealed and secured to a drug patch or may be sealed and secured to a bottom portion of the heating element compartment. The top may be integrated with the patch or may be secured to the patch or releasably secured to the patch.

The heating element compartment also provides a physical barrier limiting relative displacement of the heating element. In one embodiment, the heating element is contained within the compartment by sealing and securing at least a portion of an edge of the top. The sealed edge contains the heating element within the compartment and prevents the compartment from being unintentionally displaced out of the compartment.

Figure 15:
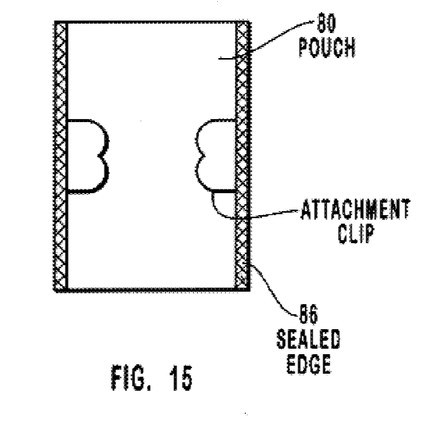
FIG. 15 shows a top view of securable compartment having attachment clips.
Figure 16:
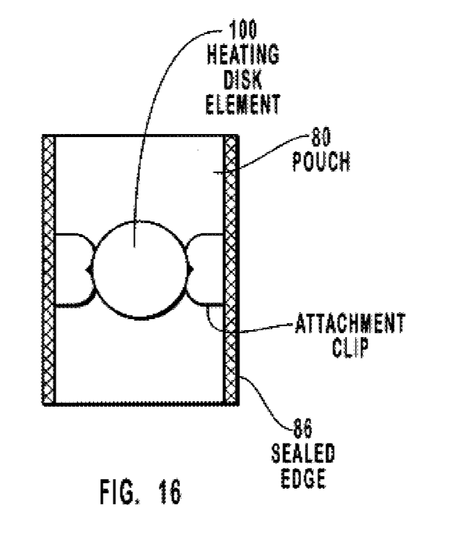
FIG. 16 shows a top view of a securable compartment having attachment clips in which the disk is held in place by the clips.
Figure 17:
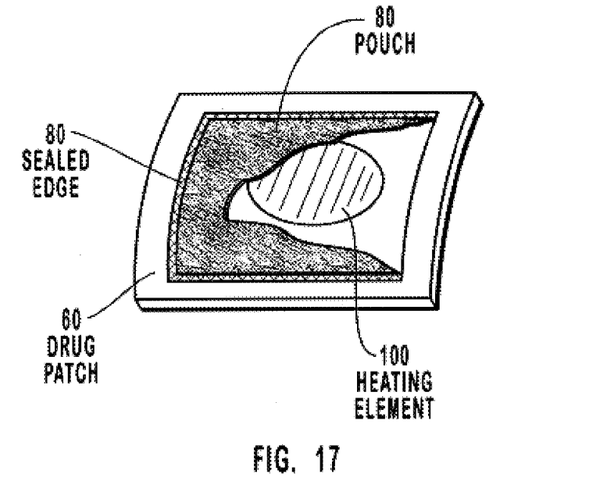
FIG. 17 is a partial cutaway of a securable compartment with a freely transferrable heating element retained in an area of retaining secured to a drug delivery patch.

Another potential means of restraint is the use of materials that have of create sufficient frictional forces between the heating element and the heating element compartment to resist the displacement and restrain the heating element in the compartment when the heating element experiences a directional force that would otherwise displace the heating element. Similarly, a clip or slide mechanism may be provided to restrain the heating element as shown in FIGS. 15 and 16. Limited adhesion or a very light weight adhesive within the heating element compartment may also provide a force, for resisting lateral displacement of the heating element.

The heating element compartment comprises at least a top for defining the compartment and at least a portion of an edge of the top that is secured. The edge may be secured to a transdermal drug delivery patch (drug patch). Alternatively, the edge may be secured to a bottom of the heating element compartment. If the top is secured to the drug patch, the top side of the drug patch may serve as a "bottom" for the heating element compartment; the top is secured at least along one edge (or a portion of one edge) to the transdermal drug patch. The top and bottom or the top and the drug patch define a heating element compartment that is secured, or is capable of being secured to or is integrated with a transdermal drug patch. Thus, the top is secured to the patch or alternatively, the top is secured to a bottom to form a pouch.

The top may have a shape that corresponds to the shape and size of the heating element to facilitate the restraint of the heating element in the restraining area of the heating element compartment. As shown in FIGS. 1 through 20, the top may be any number of shapes and sizes. The shape of the top (as well as the heating element) may be oval, circular or semicircular, polygonal, or any other number of shapes. At least one edge or a portion of one edge of the top must be sealed to the drug patch, or in the alternative, to a bottom sheet to form a heating element compartment or a pouch.

The top may be manufactured from any number of materials known in the art. The qualities of the material may affect the design of the pouch and the corresponding heating elements, and may affect or even dictate the type of treatment with which the pouch and heating element can be used. The top may be air permeable, air impermeable, or selectively permeable. It may be translucent, transparent, or be a particular color. The top may have inherent insulative properties or may be designed and manufactured to have enhanced insulative properties. The top and/or the compartment defined by the top may also protect and shield the heating element once the heating element is in place. The top may be rigid, but is preferably flexible and elastic.

Some of the embodiments of the present invention require that oxygen or air be able to pass into the heating element compartment, others do not. If the heating element does not require air to pass through into the heating element compartment in order to function, the top of the compartment can be made of a material which is air impermeable. Thus, the materials used to form the heating element compartment will depend in part upon the type of heating element selected. Characteristics of the pouch's construction may vary depending upon the use of the pouch, but the pouch should be securable or integrated with the heating patch and should allow the heating element or the pouch contents to be freely transferred into or out of the pouch at a desired time.

In one embodiment, the heat from the heating element activates adhesive on at portion of the top, such as the entry space into the pouch, and seals the pouch when that portion is closed. When the heating element stops generating heat, the adhesive is deactivated and the pouch opens or is more readily opened along that portion.

The freely transferrable heating element of the present invention is a device capable of delivering controlled heat to the transdermal drug delivery patch and/or the patient's skin The heating element is of a size and shape that corresponds to the securable heating, element compartment. The freely transferrable heating element can be placed in the heating element compartment and remains secured in the area of restraint relative to tie drug patch. The heating element compartment reduces the likelihood that the freely transferable heating element will be unintentionally dislodged until the heating element is intentionally removed from the compartment and drug patch. The heat from the heating element can be generated using a chemical reaction, such as an oxidation reaction, electrical heat, or other means of generating controlled thermal heat. Other methods for generating heat, such as crystallization, microwave, or infrared heat, are also contemplated.

The heating element may provide insulation to the drug patch and skin, and may be designed to provide additional insulation to maintain a higher, controlled temperature. The heating element shapes and sizes may correspond to the shape and sizes of the heating element compartment and have substantially similar dimensions. The heating element is designed to allow the heating element to be placed within the heating element compartment with relative ease and to be removed from the compartment with relative ease, but nonetheless remains secured in the compartment to reduce the likelihood the heating element will be unintentionally displaced from the compartment or separated from the patch.

The heating element of the present invention can provide heat for a particular duration. Where the heating element is an electrical heating element the duration of the heat may be any amount of time limited only by the ability of the battery or electric power supply to supply current to the electrical heating element. The electrical heating element can pulse on and off as necessary and the replacement drug patches can be supplied as frequently as necessary. Heating elements that use chemical reactions can be designed, manufactured to provide heat for a given duration.

The heating element provides controlled heating. Controlled heating allows the user to provide a level of heat that results in an increase in temperature to a predetermined or prescribed range. Controlled heating is preferable to heating devices that are not controlled. If the heating element is incapable of delivering controlled heat, it becomes difficult to regulate the amount of drug being delivered, and the potential for overdose or underdose is significantly increased. Similarly, the patient's skin may be blistered or burned by uncontrolled heat. By being secured in the area of restraint within the compartment attached to the patch, the heating element provides uniform, controlled heating.

One embodiment of the heating element comprises a chamber defined by air impermeable walls. The chamber is defined by a bottom wall, a top wall and side walls. The heating element preferably comprises the composition of activated carbon, iron powder, sodium chloride, water, and optionally, sawdust, which is disposed in the chamber. The top wall is preferably a flexible air impermeable material having a plurality of holes therethrough. The top wall may be an air permeable membrane or an air impermeable material with a plurality of holes. The top wall can have at least one covering for the plurality of holes or can have a covering to prevent air from passing through the air permeable membrane. In the embodiment having a plurality of holes in the top wall, the to holes can be selectively covered and uncovered. By selectively coveting and uncovering the holes in the top wall, the heat and duration may be varied and administered as desired.

The present invention can be used to increase the serum concentration of the drug delivered by the drug patch by a desired amount. For example, it may be necessary in treating a particular patient to increase the serum concentration of the drug delivered by the drug patch by 10% over the normal serum concentration as established by the drug patch's steady state. The present invention allows a controlled increase in temperature, which can be maintained at the increased level and if desired, returned to the original steady state level without changing the drug patch used to deliver the drug. Similarly the patient may find that an increase of a certain percentage is necessary for certain activities. A patient may need an increase in a drug serum concentration level during a period of increased physical activity or may require less drug during a period of rest. The present invention provides the capacity to conveniently adjust drug serum concentration levels by applying controlled heat and does so in a way that limits the chances that the drug patch will be dislodged or compromised during the application.

The securable heating element compartment can lee integrated with a specially designed drug patch, or used in conjunction with drug patches known in the art. Where the drug patch is integrated with the heating element compartment, it may be advantageous to only use a top to form the securable compartment. Where the patch is a pre-existing patch or one available in the market, the top sheet may need to be combined with a bottom sheet to form a securable heating element compartment. The securable heating element compartment should be of a shape and size to correspond to the specific drug patch.

The heating element should be of a shape and size to conform or correspond to the heating element compartment and the heating element should be designed for safe and effective use with a particular type of drug patch. For example, the freely transferable heating elements designed for use with transdermal fentanyl may have a particular size and shape and color. For a patch with a different drug, such as a testosterone patch, the colors and shapes of the heating element may be different than those for fentanyl. Thus, it is preferable that the shapes and sizes of the securable heating element compartments, and in particular the heating elements, be designed and manufactured so that the compartments and heating elements designed for use with one type of drug patch are not readily useable or interchangeable with another type of drug patch. The color may indicate the type of drug with which the securable compartment and heating element should be used and may also indicate the desired effect the compartment and heating element are intended to have If a securable compartment and heating element is designed for a particular drug patch and if use of the heating element with a different drug patch could cause harm or overdose, the heating element and corresponding compartment should be designed so as not to be compatible with the drug patches that could result in such harm.

The present invention allows for heating elements and other articles to be placed proximate to a transdermal drug patch using a heating element compartment or pouch. For example, the compartment or pouch could be used to retain various devices which could be advantageously placed proximate to the drug delivery patch, such as iontophoresis devices, timing devices, notification or reminder devices, any type of heating and/or cooling mechanisms, patient or patch monitoring devices, alarms, timers, watches, microprocessors, thermostats, thermometers, use indicators, and potentially and various novelty items such as toys for encouraging the use of the delivery system by children.

It is understood that a considerable variety of drug classes and specific drugs can be used with the present invention.

Drug classes may include without limitation androgens, estrogens, nonsteroidal anti-inflammatory agents, antihypertensive agents, analgesic agents, antidepressants, antibiotics, anticancer agents, local anesthetics, antiemetics, antiinfectants, contraceptives, antidiabetic agents, steroids, anti-allergy agents, anti-migraine agents, agents for smoking cessation, and anti-obesity agents. Specific drugs include without limitation nicotine, testosterone, estradiol, nitroglycerine, clomidine, dexamethasone, wintergreen oil, tetracaine, lidocaine, fentanyl, sufentanil, progesterone, insulin, vitamin A, vitamin C, vitamin E, prilocaine, bupivacaine, sumatriptan, dihydroergotamine, and scopolamine.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

FIG. 7-A shows a five-sided top with three edges suitable for sealing;

FIG. 7-B shows a one-sided top with a portion of an edge suitable for sealing;

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, as represented in FIGS. 1 through 20, is not intended to limit the scope of the invention, as claimed, but is merely representative of the presently preferred embodiments of the invention.

The presently preferred embodiments of the invention will be best understood by reference to the drawings, wherein like parts are designated by like numerals throughout.

Figure 1:
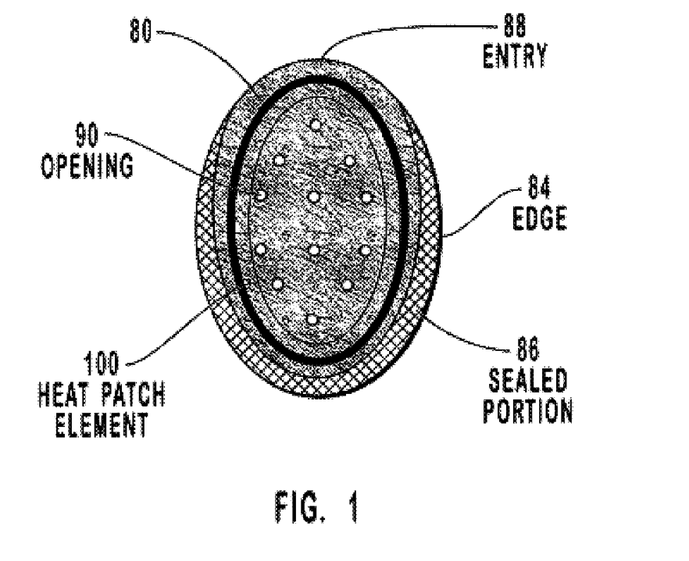
FIG. 1 shows a top view of a drug patch with a securable compartment and a freely transferrable heating element.
Figure 2:
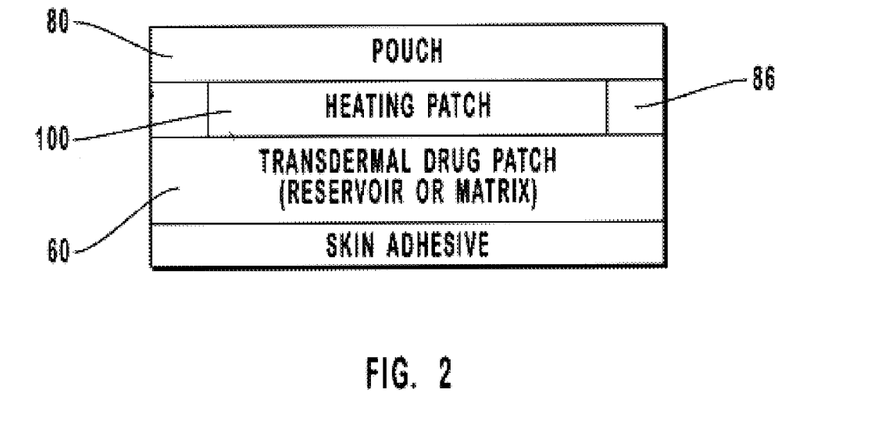
FIG. 2 is a cross section of the drug patch with the securable compartment and freely transferrable heating element.
Figure 3:
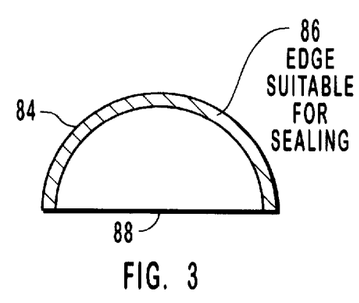
FIG. 3 shows an embodiment of a two-sided top with at least one edge suitable for sealing.
Figure 4:
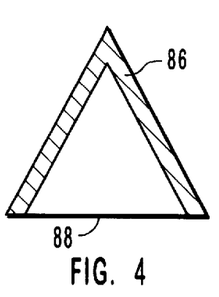
FIG. 4 shows a top having three edges with at least two edges suitable for sealing.
Figure 5:
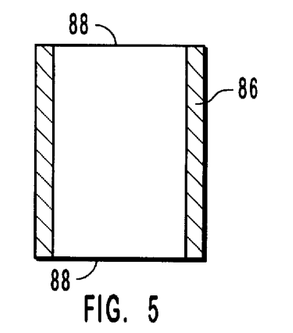
FIG. 5 shows a four-sided top having two edges suitable for sealing.
Figure 6:
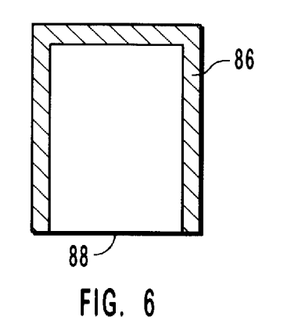
FIG. 6 shows a top having four edges with two edges suitable for sealing.
Figure 7A:
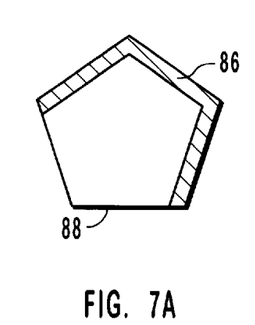
Figure 7B:
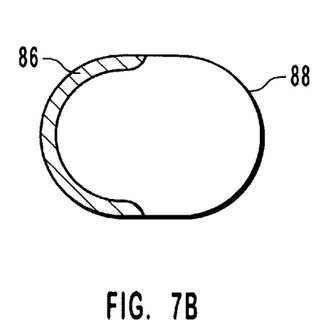
Figure 8:
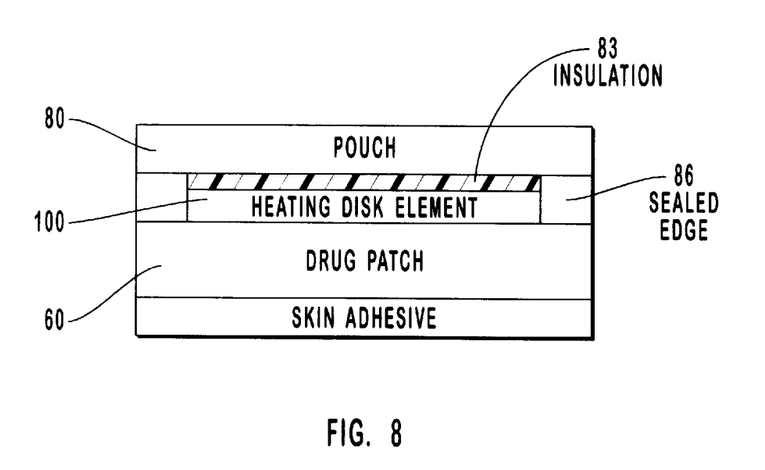
FIG. 8 shows a cross section of the securable compartment with a freely transferrable heating element secured on a heating patch, the heating element and the compartment having additional insulative properties.
Figure 9:
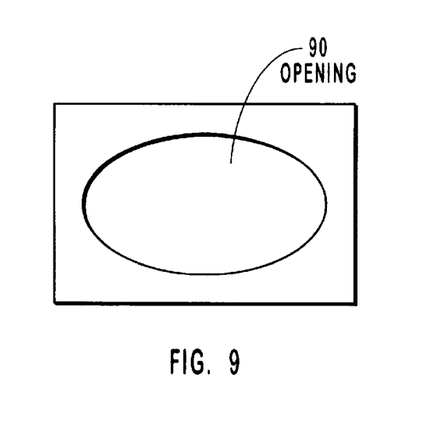
FIG. 9 shows a top defining an opening.
Figure 10:
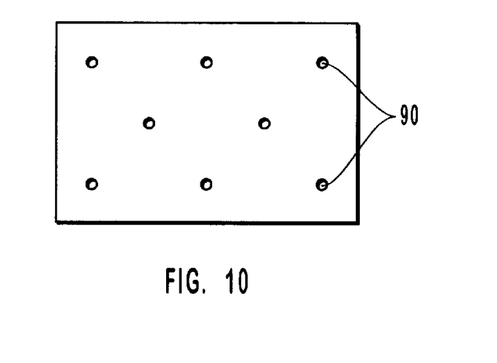
FIG. 10 shows a top defining a plurality of openings.
Figure 11:
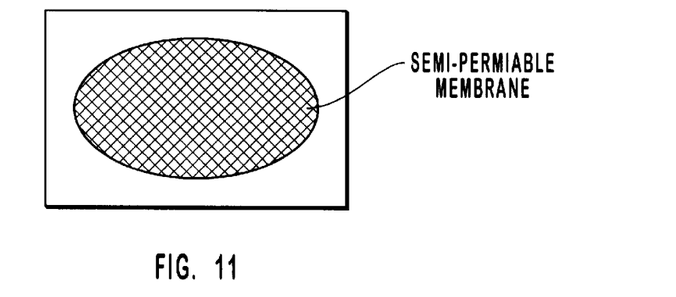
FIG. 11 shows a top defining an opening having a semi-permeable membrane covering said opening.
Figure 12:
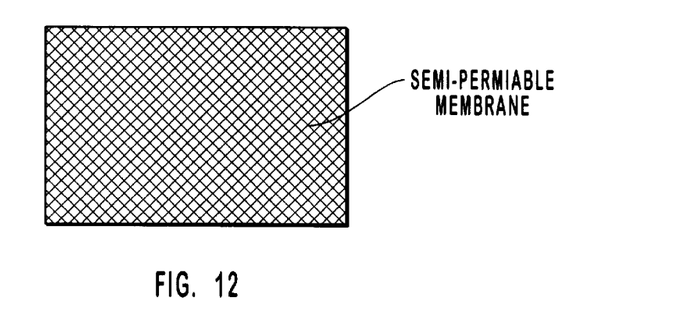
FIG. 12 shows a top that is an air permeable membrane.
Figure 13:
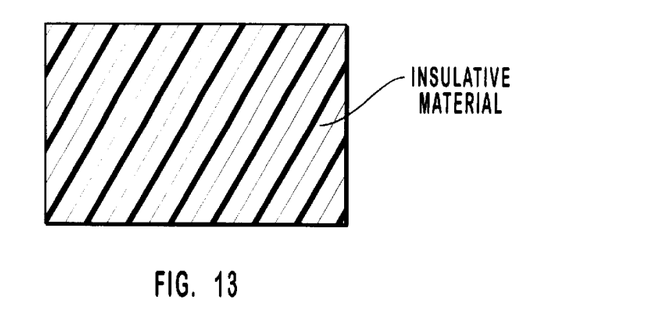
FIG. 13 shows a top that has additional insulative properties.

As shown in FIG. 1, in one embodiment, the present invention comprises a drug delivery patch 60, a securable heating element compartment 80, and a freely transferrable heating element 100 retained in compartment 80. The drug patch 60, with a heating element compartment 80 and an electric heating element 100, is placed upon the skin of a patient in need of transdermal delivery of a drug where heating element 100 delivers controlled heat to the patient's skin and the drug formulation and the drug delivery patch 60. The controlled heat increases the absorption of the drug through the skin into the systemic circulation of the patient. Controlled heat on the patient's skin and drug patch 60 results in an increased absorption rate that allows the patient to obtain a steady state concentration in the systemic circulation more quickly than the patient could without the heating element.

After the heating is finished, heating element 100 may be removed, but is preferably left inside securable heating element compartment 80 in order to provide insulation to the administration site. Heating element 100 can be replaced with another freely transferable heating element 100 if necessary in order to provide additional heat. The additional heat may be provided to further increase the concentration level of the steady state, or alternatively, may be provided to give the patient additional drug beyond a desired steady state. After establishing a steady state, original heating element 100 can be replaced by a different kind of heating element 100, if necessary, and a different level of controlled heat may be applied to the patient's skin, the dermal drug patch 60, and the drug formulation in order to cause a sharp increase in the drug concentration above the steady state. Such a dramatic rise in the increase may help to improve a patient's treatment such as by mimicking natural circadian patterns, providing additional relief for breakthrough pain, or providing additional drug when a patient has a heightened need (urgent need) or is experiencing withdrawal pains or cravings (breakthrough cravings).

Figure 19:
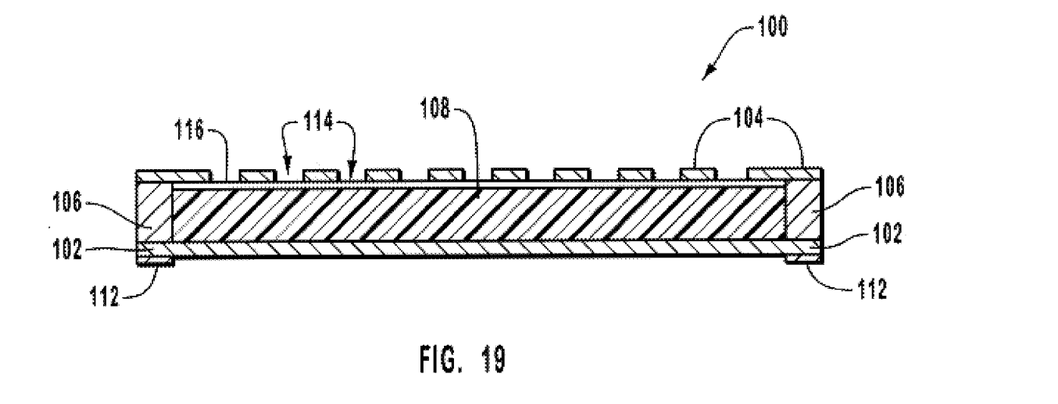
FIG. 19 shows an embodiment of an exothermic heating element.
Figure 20:
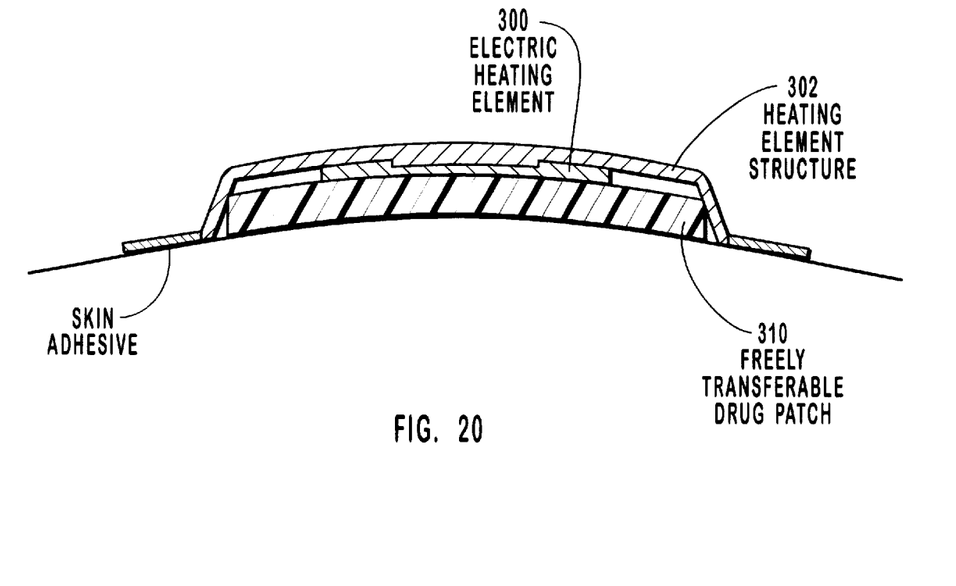
FIG. 20 shows another embodiment of the present invention.

In one embodiment of the present invention, controlled heating of the heating element is provided by an oxidation reaction. As shown in FIG. 19, the heating element 100 comprises side wall 106 defined by a ⅛ inch thick rectangular foam tape (2 layers of No. 1779 ¹⁄₁₆" white foam tape, 3M Corporation, Minneapolis, Minn., USA) with an outer dimension of about 2.25 inches by 4 inches with an opening therein having an inner dimension of about 1.75 inches by 3.5 inches, a bottom wall 102 comprising rectangular medical tape (No. 1525L plastic medical tape, 3M Corporation, Minneapolis, Minn., USA) of a dimension of about 2.25 inches by 4 inches with a non-adhesive side attached to the bottom of side wall 106, and a top wall 104 comprising a rectangular 1/32 inch thick foam tape (No. 9773 1/32" tan foam tape, 3M Corporation. Minneapolis, Minn., USA) with forty-five holes 114 (diameters approximately 0.9 mm, in a 5 by 9 pattern with about 7.5 mm to 8.0 mm center spacing) therethrough. Side wall 106, bottom wall 102, and top wall 104 define a chamber. The holes 114 of top wall 104 may be covered by an air permeable membrane 116 comprising a porous membrane (No. 9711 microporous polyethylene film—CoTran™, 3M Corporation, Minneapolis, Minn., USA) disposed between the top wall 104 and the temperature regulating mechanism 108. Side wall 106, bottom wall 102, and top wall 104 all have 1/8 rounded corners. Heat generating component 108 disposed in the chamber comprises a mixture of activated carbon (HDC grade—Norit Americas, Inc., USA), iron powder (grade R1430—ISP Technologies, USA), saw dust (Wood Flour, Pine—Pioneer Sawdust, USA), sodium chloride and water in the weight ratio of approximately 5:16:3:2:6 weighing approximately 16.5 grams. Heating element 100 is sealed in an air-tight container immediately after fabrication.

In one embodiment, the invention entails the integral attachment of heating element compartment 80 (or pouch 80) to the top side of a transdermal drug delivery patch 60 for the purposes of affixing controlled heating element 100, such as a heating disc 100, to drug patch 10. Drug patch 60 may be a reservoir or matrix (monolith) patch. The compartment or pouch 80 is formed by securing a heating element compartment top 82 to a drug patch 60. Top 82 has at least one edge 84 with at least a portion 86 of edge 84 being secured or sealed to drug patch 60. Pouch 80 may be made of a variety of materials. Top 82 of pouch 80 may be attached to drug patch 60 along at least portion 86 of edge 84 by any of several means such as heat-sealing, RF-welding, or the use of any variety of adhesive. Pouch 80 is used to house or contain heating element 100, (such as a disposable, air-activated, chemical heating or disc to enhance the delivery of drugs through the skin manufactured by ZARS) holding the heating element 100 in direct contact with drug patch 60. The perimeter of "marsupial" pouch 80 is sealed to drug patch 60 except for an entry 88 large enough to slide heating element 100 in and out of pouch 80. Sealed edges 86 near entry 88 of the pouch 80 provide a smooth pathway for easy insertion and removal of heating element 100. (See FIG. 19). Pouch 80 defines at least one opening 90 or a number of smaller openings 90 across its surface in order to allow oxygen to enter and activate heating element 100.

The active ingredient in transdermal drug patch 60 may be any of a number of drugs, such as, but not limited to, fentanyl, testosterone, estradiol, scopolamine, nicotine, nitroglycerin, local anesthetics etc. Transdermal drug patch 60, attached pouch 80, top 82, and heating element 100 may be any of a variety of different shapes, such as, but not limited to, a square, rectangular, circular, oval, triangular, as shown in FIGS. 1–20.

The use of different heating elements 100 with different heating characteristics can provide important advantages in treatments. For example, with the transdermal delivery of fentanyl, the application of a 4-hour heating element with a temperature of 42–44° C. has been found to decrease the time required for patch 60 to react steady-state serum fentanyl concentrations from 14–18 hours to 3–4 hours. After steady-state drug levels have been achieved, patients often experience short episodes of increased pain known as breakthrough pain. A 5-minute application of similar heating element 100 has been found to increase serum fentanyl levels by more than 60 percent. This increase is more than sufficient to combat breakthrough pain. Hence, at least two different types of heating elements 100 or discs 100 are useful in conjunction with the transdermal fentanyl patch 60; one for reducing the onset time to steady-state levels and one for combating breakthrough pain.

Heating elements 100 of different sizes and shapes and different heating temperatures and durations may be housed in marsupial pouch 80. Heating patches 100 or discs 100 may be color-coded in order to indicate different heating temperatures and durations for different uses. For example, the onset heatings, element 100 might maintain a temperature of 42–44° C. for 4-hours and might be blue. The breakthrough heating element 100 might maintain a temperature of 42–44° C. for 5–20 minutes and might be green.

In the case of fentanyl, fentanyl patch 60 may be packaged with a blue onset heating element 100 already housed in marsupial pouch 80. Thus, when patch 60 is applied, the heating begins and a shorter onset time to steady-state is achieved. After several hours, when heating element 100 has expired and steady-state has been reached, the heating element 100 may be left in marsupial pouch 80 in order to provide a level of insulation, which may protect drug patch 60 from variations in ambient temperature. Later on, when an episode of breakthrough pain is experienced, blue onset heating element 100 may be removed from marsupial pouch 80 and a green breakthrough heating element 100 may be inserted into pouch 80. As heating element 100 dies out on its own after its prescribed heating duration, it is not necessary to remove it at specified time intervals. Rather, heating element 100 may be left in marsupial pouch 80, if desired, until a new breakthrough heating element 100 is needed.

There are several significant advantages to "marsupial" pouch technology. Since marsupial pouch 80 is directly attached to transdermal drug patch 60, there is no need to use adhesive to attach heating element 100 to drug patch 60, which would increase the likelihood of removing drug patch 60 upon removal of the heating element 100. Marsupial pouch 80 provides excellent contact between heating element 100 and drug patch 60. Marsupial pouch 80 limits the risk of abuse of heating patch 60 with other drug patches for which it is not indicated and with which it has not been studied. As heating elements 100, or discs 100, are preferably not adhesive, they cannot be used with any drug patch, but only with those that have a corresponding pre-attached marsupial pouch 80 for housing drug patch 60. Marsupial pouch 80 simplifies the process of using several different types of heating elements 100 (for example, onset and breakthrough elements) since it is simple and easy to remove and replace heating elements 100. Heating, elements 100 may have a tab on one end to facilitate easy insertion and removal.

EXAMPLE 1

In one example, an embodiment of the present invention is used for dermally administrating nicotine for suppressing a patient's nicotine cravings. A user (a patient or caregiver) administers a nicotine patch 60 with a freely transferrable heating element 100 in a heating element compartment 80 secured to patch 60. After just a few hours, the patient should obtain a steady state nicotine concentration in the blood stream sufficient to suppress a baseline nicotine craving. When the patient starts to have an episode of increased nicotine craving (a breakthrough craving), the user replaces freely transferrable heating element 100 within a second, different transferrable heating element 100, the second heating element having different heating characteristics. Second heating element 100 is placed in compartment 80. Second heating element 100 may use an exothermic reaction to generate heat. The heat created by second heating element 100 lasts for at least 15 minutes before the exothermic reaction exhausts second heating, element 100. The heat increases the transport of nicotine across the skin and increases the blood flow in the tissues under nicotine patch 60, which carries the nicotine stored in tissues under patch 60 into the systemic circulation at increased rates. As a result, the patient gets a rapid increase in blood nicotine concentration to treat the surge of the nicotine craving. After the heating, the absorption rate gradually declines to deliver the steady state nicotine concentration in the blood stream.

EXAMPLE 2

Another example of using an embodiment of the present invention for dermally administering testosterone to increase and optimize the amount of drug delivered comprises a user placing a testosterone patch 60, such as a one day dermal testosterone patch (EG Androderm® produced by TheraTech, Inc. of Salt Lake City, Utah, USA) on the skin of the patient. Patch 60 can be applied to the skin at night, for example, around 10:00 p.m. However, in order to raise the steady state concentration of the testosterone quickly, the user may apply a freely transferrable heating element 100 to a heating element compartment 80 secured to testosterone patch 60. Heating element 100 is designed to provide heat for a desired period of time in order to allow the serum. concentration of testosterone to reach a steady state more rapidly than it would without heating element 100. When heat from heating element 100 is terminated, heating element 100 may provide a measure of insulation to maintain an increased level of absorption from patch 60 or may be freely removed from compartment 80.

Testosterone patch 60 can be worn or applied at night, for example, around 10:00 p.m. However, if the patient does not get a sufficient dosage of testosterone by the next day, the user can apply a second, different heating element 100 into secured compartment 80 of patch 60. Second heating element 100 can provide increased temperature to patch 60 and the skin and the tissues under the skin and thereby significantly increase the absorption of testosterone. Additionally, the heat may promote the effectiveness of a permeation enhancer in the drug formulation of patch 60. The ultimate result is that the patient gets sufficient testosterone from patch 60 in an efficient manner. The efficient use of heating, element 100 may allow the reduction of permeation enhancer concentration in the drug formulation of patch 60. Permeation enhancers are sometimes associated with significant skin irritation.

EXAMPLE 3

The present invention can also be used to administer a drug transdermally that otherwise would have a diffusion coefficient or a permeability coefficient across a rate limiting membrane 62 of patch 60 that would be disadvantageously low. A user places a patch containing a drug onto the skin of the patient and alter waiting for a period of time to determines that the administration requires a higher concentration of drug in the patient's blood stream to properly treat the patient's condition. The user can remove freely transferrable heating element 100 and replace it with a second, different freely transferrable heating element 100 having heating characteristics that facilitate increased absorption of the drug. Increased temperature provided by second heating element 100, for example, may increase the diffusion coefficient of the active ingredient in the formulation and/or increase the permeability coefficient of the drug across the rate limiting membrane of patch 60. The overall rate at which the active ingredient enters the body would thereby also increase and in turn, increase the concentration of the active ingredient in the patient's blood stream.

EXAMPLE 4

The present invention can be used to decrease the onset time of a drug from a transdermal Druid patch 60. A user places patch 60 on a patient's skin. Patch 60 contains a freely transferrable heating element 100 secured in heating element compartment 100 on patch 60. The heat allows the drug formulation in transdermal drug patch 60 to be absorbed more quickly through the skin. However, if the user determines that a faster onset time is necessary for proper treatment of the patient, the user can replace the initial heating element 100 with a second, different freely transferrable heating element 100 having different heating characteristics, for example, generating higher temperatures. The increased temperature allows the drug to be absorbed into the patient's systemic circulation more quickly and if sustained over a sufficient amount of time results in a quicker onset of the drug. After obtaining onset in a shortened period of time, second heating element 100 with the higher temperature can be left in place for insulative effect or removed or replaced with a heating element 100 that allows patch 60 to deliver the drug at a more typical steady state. The important advantage provided by this approach is that the onset time of patch 60 can be shortened without significantly altering the patch's steady state delivery rate.

EXAMPLE 5

Another example of the present invention is used to provide a deeper penetration of a drug formulation into a patient's tissues. The user places a transdermal drug patch 60 on the skin of the patient. Drug patch 60 contains a freely transferrable heating element 100 in a heating element compartment 100 secured to patch 60. Patch 60 heats the patient's skin and heating element 100 for a period of time. The drug from transdermal patch 60 is absorbed into the tissues beneath and proximate to drug patch 60. Heating element 100 facilitates the absorption of the drug into the tissue.

If it is determined that the drug is not penetrating beneath the surface of the skin deeply enough for proper treatment, heating element 100 can be removed and replaced with a second, different freely transferrable heating element 100, which provides different heating characteristics, such as increased duration or increased temperature. For example, as second heating element 100 increases the temperature of the drug formulation and the tissues around drug patch 60, the heat drives the drug further into the skin and allows for deeper penetration.

If desired, after the drug has reached a penetration level sufficient for the treatment, second heating element 100 can be removed and replaced with the original heating element 100 or another freely transferrable heating element 100 having heating characteristics more suited toward delivering a drug at a desired rate.

EXAMPLE 6

Another example of the present invention comprises replacing an original heating element 100 with a second, different heatings element 100 to increase solubility of the drug in formulation. A drug delivery patch 60 may have a drug formulation with a certain solubility of the drug in the drug formulation. The solubility rate may be appropriate for a given treatment and provide the drug to the skin for absorption at a particular desired rate. Solubility of the drug may be dependent upon the heat applied to the drug formulation by an initial freely transferrable heating element 100. In the present invention, initial heating element 100 can be removed and replaced with a second, different, freely transferrable heating element 100 that provides different heating characteristics. Second heating element 100 may generate increased heat so that the solubility of the drug in the drug formulation is higher. Because the increased temperature increases the solubility of the drug compound in the formulation, more drug compound can be dissolved in the formulation, which may yield a higher driving force for the transdermal permeation of the drug compound. Ultimately, more of the drug can enter the patient's systemic circulation.

EXAMPLE 7

Figure 18:
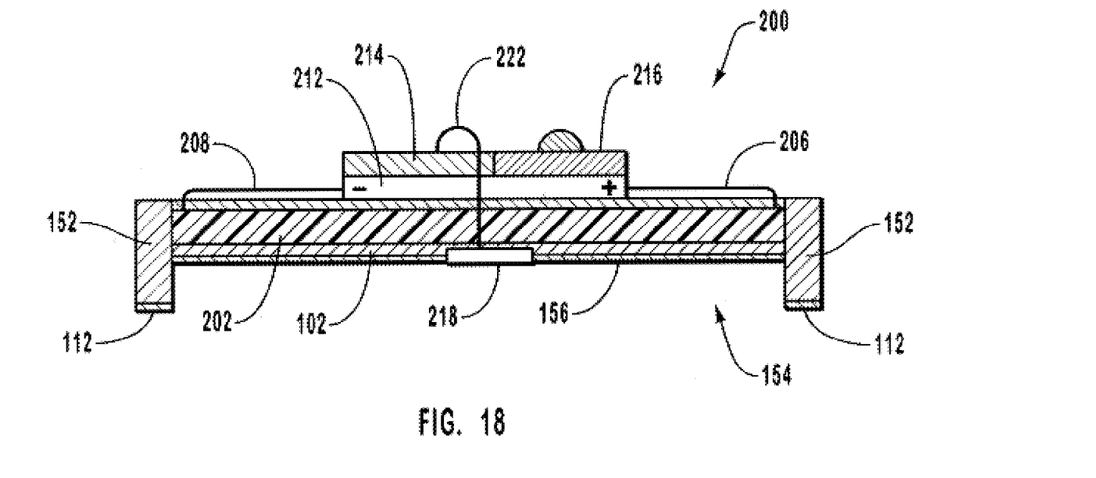
FIG. 18 shows one embodiment of an electric heating element.

As mentioned above, the possible heating elements are not limited to the exothermic reaction mixture of iron powder, activated carbon, salt, water, and sawdust, as discussed above. FIG. 18 illustrates an electric heating element 200 comprising an electric heating element 202 surrounded by a bottom wall 102, a top wall 104, and side walls 152 The side walls 152, preferably, extend a distance below the bottom wall 102 to define a cavity 154. It is understood that the electric heating element 202 does not have to have the side walls 152 forming a cavity 154.

The bottom wall 102 and the side walls 152 are preferably made of a flexible non-air permeable material, such as non-air permeable closed-cell foam material. A portion of the bottom of the heating element 200 includes an adhesive material 112 on the bottom of the side walls 152 and, preferably, includes a second adhesive material 156 in the bottom of the bottom wall 102, wherein the second adhesive material 156 is preferably less adhesive than the adhesive material 112. The electric heating element 202 preferably comprises a flexible resistor plate that can generate heat when supplied with an electric current through traces 206, 208. The electric current is preferably supplied from a battery 212 attached to a control mechanism 214, and an electronic switch 216. The battery 212, the control mechanism 214, and the electronic switch 216 are preferably attached to the top surface of the top wall 104. The electric heating element 202 is activated by triggering the electronic switch 216 which begins the flow of electric current from the battery 212 to the electric heating element 202. A temperature sensor 218, such as a thermistor, is preferably attached to the bottom of the bottom wall 102 and sends a signal (corresponding to the temperature at the bottom of the bottom wall 102) through electric trace 222 to the control mechanism 214. The control mechanism 214 regulates the flow of current to the electric heating element 202, so that the electric heating element 202 quickly brings the temperature at a contact surface between the bottom wall 102 and a top of a drug patch (not shown) to a pre-determined level and maintains the temperature at that pre-determined level. The following features may be incorporated into the control mechanism 214: 1) a mechanism that allows a physician or care giver set the length of each heating period for each patient, which allows the physician to limit the heating, and hence the extra drug that the patient can get based on the conditions of the patient; 2) a mechanism that allows the physician or care giver to set the minimum time between the heating periods, and hence how often the patient can get the extra drug through increase heat; 3) a mechanism that allows the physician or care giver to set a predetermined temperature; and/or 4) a mechanism that allows the physician or care giver to control the heating temperature profile, such as gradually increasing heating temperature or decreasing temperature over a pre-determined period of time. These features can potentially give a prior art drug patch a variety of control options for the physician and/or the patient on the quantity and timing of the delivery of extra drug. The heating element can be freely transferable into and out of a heating element compartment or pouch.

Figure 14:
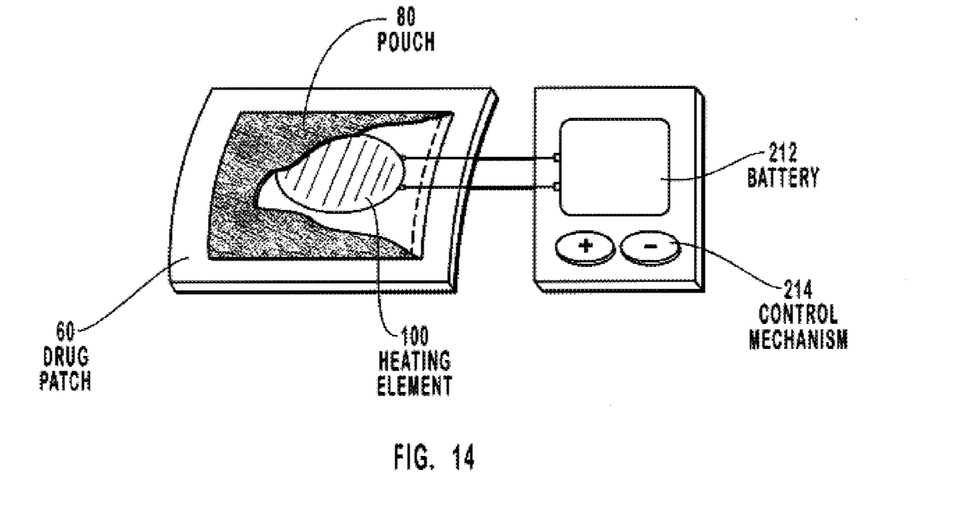
FIG. 14 shows an electrically operated heating element in a securable compartment attached to a transdermal drug patch.

Battery 212, control mechanism 214, and electric switch 216 may be attached to the heating element or the drug delivery patch to which the heating element is secured. Alternatively, battery 212 and control mechanism 214 may be worn separately. For example, a detached battery 212 and control mechanism 214 are shown in FIG. 14.

In another embodiment, electric heating compartment 202 may be activated by the automatic triggering of electronic switch 216 and allowing a flow of electric current from the battery through the heating element. Temperature sensor 218 that provides precise regulation of the heat generated in the heating element relay also provide an additional control mechanism for the duration of the heat generated by electric heating element 200. The electric heating element can be combined with a microprocessor 230 to provide highly accurate and highly regulated temperature control. For example, microprocessor 230 can regulate when the heating element 200 is turned on, its temperature, and when heating element 200 is turned off. Electric heating element 200 can be freely transferred from heating element compartment 80 secured to patch 60 and replaced with different electric heating element 200 or some other heating elements 100.

EXAMPLE 8

One of the distinct advantages of the present invention is the ability to use various types of heating elements 100 to generate heat for the delivery of the drug through transdermal patch 60. For example, a patient may have applied a dermal drug delivery patch 60 with a freely transferable heating element retained in a compartment secured to the patch. Heating element 100 may be an electric heating element 200 having an electric current supplied by a battery 212. In the event that the electric heating element 200 malfunctions or battery 212 for the patch runs out of current, electric heating element 200 can be easily removed and replaced with a different electrical heating element 200 or with a different heating element 100, such as a heating element using heat generated from an exothermic chemical reaction. The ability to change from electrical to exothermic chemically generated heat may be particulary advantageous where the activities of the patient prohibit or make impractical the use of a given type of heating element. Where a patient is intending to engage in an activity that would not be conducive to the use of an electrical heating element, the patient may replace the electrical heating element with the exothermic chemical heating element or some other type of heating element 100,

EXAMPLE 9

In an alternative embodiment of the present invention, a dermal drug delivery system comprises a heating element structure 302 releasably secured to a patient's skin. The heating element structure comprises a heating element 300 and a top side 304 having at least a portion of an edge secured to the skin or alternatively secured to a bottom side that is secured to the skin. Alternatively, at least two walls extending from the top side toward the bottom side may be attached to a patient's skin. Heating element structure 302 defines a compartment in which is provided an area of containment beneath the bottom side of the heating element 300. A freely transferable drug delivery patch 310 may be placed into the compartment beneath heating element 300. The drug delivery patch 310 is secured in the area of containment and maintains contact with the patient's skin to deliver the drug in the drug patch 310. Heat from heating element 300 is used as disclosed in the application to improve the administration of the drug from drug patch 310. Thus heating element structure 302 forms a drug delivery patch compartment and provides heat to drug delivery patch 310.

If heating element 300 is connected to a microprocessor, a wide variety of drug delivery patches can be used in combination with heating element 300, which can be adjusted and programmed to provide heat at desired times and for desired durations in accordance with the drug being used. Patch 310 that is used with heating element 300 could be designed to have identification information on patch 310 that indicates to the user the appropriate heat settings for heating element 300. Through the use of the microprocessor identification information is read by a reading device such as an optical scanner and the microprocessor automatically sets appropriate heating levels.

EXAMPLE 10

Another example of the present invention comprises inserting a device other than a freely transferable heating element into the drug delivery pouch. The heating element compartment provides the user the opportunity to place various devices proximate to the heating patch which can assist in dermal drug delivery. For example, an iontophoresis device can be secured to a heating patch using the pouch of the present invention. The iontophoresis device can apply a positive current from an electrode to a drug formulation on the skin that will drive positively charged ions away from the electrode and into the skin. Alternatively a negative current can be applied to influence negatively-charged ions. Current variations from the iontophoresis device will influence and increase the iontophoretic effect in drug delivery. Thus, an iontophoresis device can be placed in the heating element compartment in place of the heating element.

EXAMPLE 11

The present invention is not limited to devices which increase temperature. A cooling element may likewise decrease the temperature or cool the drug formulation, the drug delivery patch, and the patient's skin. Cooling the patient's skin may slow drug delivery in a manner that is advantageous for a given treatment. For example, the present invention can be used to increase the onset time of the drug from a transdermal drug patch 60. A user places patch 60 on a patient's skin. Patch 60 contains a freely-transferrable cooling element 100 secured in cooling compartment 100 on patch 60. The cooling element 100 is capable of cooling the drug patch 60 and the patient's skin. The cooling effect on the drug formulation in the drug patch 60 slows the absorption of the drug through the patient's skin. By slowing the absorption from the drug patch 60, the cooling element 100 reduces the serum concentration level and thereby increases the onset time of the drug.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. A transdermal drug delivery system comprising:
a dermal drug delivery patch;
a heating element compartment securable to the dermal drug delivery patch; and
an exchangeable heating element for providing heat securable within the heating element compartment.

2. The drug delivery system of claim 1, wherein said heating element compartment is defined by a top side of said compartment being sufficiently sealed to a bottom side of said compartment to retain said heating element.

3. The drug delivery system of claim 1, wherein said heating compartment is defined by a top having at least a portion of one edge sealed to dermal drug delivery patch.

4. The drug delivery system of claim 1, wherein said heating element compartment further comprises a top having at least one opening for permitting oxygen to flow into said heating element compartment.

5. The drug delivery system of claim 1, wherein said heating element compartment defines an entry for freely transferring said heating element into and out of said heating element compartment.

6. The drug delivery system of claim 1, wherein said heating element compartment provides an area for restraining said heating element.

7. The drug delivery system of claim 1, wherein said heating element is retained within said compartment using tension.

8. The drug delivery system of claim 1, wherein said heating element is retained within said compartment using friction.

9. The drug delivery system of claim 1, wherein said heating element is retained within said compartment using an attachment clip.

10. The drug delivery system of claim 1, wherein said heating element is retained within said compartment using a very light adhesive for preventing lateral movement.

11. The drug delivery system of claim 1, wherein said top of said heating compartment provides at least one sealed edge for containing said heating element within said compartment.

12. The drug delivery system of claim 1, wherein said heating element provides heat using an oxidation reaction within said heating element.

13. The drug delivery system of claim 1, wherein said heating element corresponds in size and shape to said heating element compartment.

14. The drug delivery system of claim 1, wherein said heating element provides controlled heat.

15. The drug delivery system of claim 1, wherein said heating element is an electric heating element having an electronic control mechanism.

16. The drug delivery system of claim 1 wherein said heating element is designed to provide insulative properties to the drug delivery system.

17. The drug delivery system of claim 1, wherein said heating element is an onset heating element for providing heat to improve the onset time of a drug delivery regimen.

18. The drug delivery system of claim 1, wherein said heating element is a breakthrough pain heating element for providing heat to improve drug delivery in a treatment of breakthrough pain.

19. The drug delivery system of claim 1, wherein said heating element is a breakthrough craving heating element for providing heat to improve drug delivery in a treatment of breakthrough craving.

20. The drug delivery system of claim 1, wherein said heating element is a steady state heating element for providing heat to improve a steady state drug delivery regimen.

21. The drug delivery system of claim 1, wherein said heating element is a breakthrough effect heating element.

22. A method for delivering a drug transdermally comprising the steps of:
   placing a dermal drug delivery patch upon a patient's skin at an administration site;
   securing a heating element compartment to said dermal drug delivery patch; and
   disposing an exchangeable heating element for providing heat within the heating element compartment.

23. The method of claim 22, wherein said heating element compartment is defined by a top having at least one edge sealed to a bottom.

24. The method of claim 22, wherein said heating compartment defined by a top having at least a portion of one edge sealed to the dermal drug delivery patch.

25. The method of claim 22, wherein said heating element compartment further comprises a top having at least one opening for permitting oxygen to flow into said heating element compartment.

26. The method of claim 22, wherein said heating element compartment defines an entry for freely transferring said heating element into and out of said heating element compartment.

27. The method of claim 22, wherein said heating element compartment provides an area for restraining said heating element.

28. The method of claim 22, wherein said heating element is retained within said compartment using tension.

29. The method of claim 22, wherein said heating element is retained within said compartment using friction.

30. The method of claim 22 wherein said heating element is retained within said compartment using an attachment clip.

31. The method of claim 22, wherein said heating element is retained within said compartment using a very light adhesive for preventing lateral movement.

32. The method of claim 22, wherein said top of said heating compartment provides at least one sealed edge for containing said heating element within said compartment.

33. The method of claim 22, wherein said heating element provides beat using an oxidation reaction within said heating element.

34. The method of claim 22, wherein said heating element corresponds in size and shape to said heating element compartment.

35. The method of claim 22, wherein said heating element provides controlled heat.

36. The method of claim 22, wherein said heating element is an electric heating element having an electronic control mechanism.

37. The method of claim 22, wherein said heating element is designed to provide insulative properties to the drug delivery system.

38. The drug delivery system of claim 22, wherein said heating element is an onset heating element for providing heat to improve the onset time of a drug delivery regimen.

39. The drug delivery system of claim 22, wherein said heating element is a breakthrough pain heating element for providing heat to improve drug delivery in a treatment of breakthrough pain.

40. The drug delivery system of claim 22, wherein said heating element is a breakthrough craving heating element for providing heat to improve drug delivery in a treatment of breakthrough craving.

41. The drug delivery system of claim 22, wherein said heating element is a steady state heating element for providing heat to improve a steady state of a drug delivery regimen.

42. The method of claim 22, wherein said heating element is a breakthrough effect heating element.

43. The method of claim 22, further comprising the steps of removing said heating element from the heating element compartment and replacing said heating element with a freely transferrable second heating element in the heating element compartment.

44. The method of claim 43, further comprising the steps of heating said dermal drug delivery patch and the skin of a patient with said second heating element to provide faster onset.

45. The method of claim 43, further comprising the steps of heating said dermal drug delivery patch and the skin of a patient with said second heating element to provide relief from breakthrough pain.

46. The method of claim 43, further comprising the steps of heating said dermal drug delivery patch and the skin of a patient with said second heating element to provide relief from breakthrough cravings.

47. The method of claim 43, further comprising the steps of heating said dermal drug delivery patch and the skin of a patient with said second heating element to provide relief from breakthrough effects.

48. The method of claim 43, further comprising the steps of heating said dermal drug delivery patch and the skin of a patient with said second heating element to provide deeper drug penetration.

49. The method of claim 43, further comprising the steps of heating said dermal drug delivery patch and the skin of a patient with said second heating element to provide drug serum concentration levels that mimic a patient's circadian period.

50. A method for delivering a drug transdermally comprising the steps of:
   placing a dermal drug delivery patch upon a patient's skin at an administration site;
   securing a cooling element compartment to said dermal drug delivery patch; and
   disposing a exchangeable cooling element within the cooling element compartment.

51. A method for delivering a drug transdermally comprising the steps of:
   placing a dermal drug delivery patch upon a patient's skin at an administration site;
   securing an iontophoresis device compartment to said dermal drug delivery patch; and
   disposing an iontophoresis device within the iontophoresis compartment.

52. A method for transdermally delivering a drug comprising the steps of:
   securing a heating element structure on a patient's skin, said heating element structure comprising a heating element disposed above the patient's skin and defining a drug patch compartment; and
   disposing a dermal drug patch within said drug patch compartment, said drug patch being proximate to and capable of being heated by said heating element, and said drug patch being exchangeable into and out of the drug patch compartment.

* * * * *